United States Patent
Ding et al.

(10) Patent No.: US 10,664,494 B2
(45) Date of Patent: May 26, 2020

(54) METHOD AND SYSTEM FOR SYNCHRONOUSLY STORING MULTI-MODAL INFORMATION OF PORTABLE ENDOSCOPE

(71) Applicant: Hefei University of Technology, Hefei, Anhui (CN)

(72) Inventors: Shuai Ding, Anhui (CN); Shanlin Yang, Anhui (CN); Qiang Fu, Anhui (CN); Lin Zhang, Anhui (CN)

(73) Assignee: Hefei University of Technology, Hefei (CN)

( * ) Notice: Subject to any disclaimer, the term of this patent is extended or adjusted under 35 U.S.C. 154(b) by 0 days.

(21) Appl. No.: 16/049,709

(22) Filed: Jul. 30, 2018

(65) Prior Publication Data

US 2019/0034509 A1 Jan. 31, 2019

(30) Foreign Application Priority Data

Jul. 31, 2017 (CN) .......................... 2017 1 0640588

(51) Int. Cl.
*G06F 16/27* (2019.01)
*H04L 29/08* (2006.01)
(Continued)

(52) U.S. Cl.
CPC .......... *G06F 16/275* (2019.01); *G06F 16/178* (2019.01); *G16H 40/63* (2018.01);
(Continued)

(58) Field of Classification Search
CPC .................................................... G06F 16/275
(Continued)

(56) References Cited

U.S. PATENT DOCUMENTS

2012/0162401 A1* 6/2012 Melder ................ H04N 7/183
348/65
2015/0296015 A1 10/2015 Lin et al.
(Continued)

FOREIGN PATENT DOCUMENTS

CN 105335611 A 2/2016
CN 105530284 A 4/2016
(Continued)

*Primary Examiner* — Syling Yen
(74) *Attorney, Agent, or Firm* — Wayne & Ken, LLC; Tony Hom (57) ABSTRACT

The present invention provides a method and system for synchronously storing multi-modal information of portable endoscope. The method includes: S1: when a mobile terminal acquires data collected by a portable endoscope and updates local data with the acquired data, acquiring update record of the local data of the mobile terminal; and, S2: when the mobile terminal is synchronized with a cloud, synchronizing data in the mobile terminal with data in the cloud by using the update record as information to be synchronized. By creating a table to be synchronized to store change information and location information of files and selectively performing synchronization from the mobile terminal to the cloud or from the cloud to the mobile terminal according to whether or not the table to be synchronized is null during synchronization, unnecessary synchronization operations, storage burden of the mobile terminal and synchronization time and traffic are all reduced.

8 Claims, 4 Drawing Sheets

(51) Int. Cl.
*G16H 40/63* (2018.01)
*G16H 40/67* (2018.01)
*G06F 16/178* (2019.01)

(52) U.S. Cl.
CPC ......... *G16H 40/67* (2018.01); *H04L 67/1095* (2013.01); *H04L 67/12* (2013.01)

(58) Field of Classification Search
USPC ........................................................ 707/610
See application file for complete search history.

(56) References Cited

U.S. PATENT DOCUMENTS

2016/0019233 A1* 1/2016 Wijayaratne ...... G06F 17/30174
 707/625
2017/0193163 A1* 7/2017 Melle .................... G06F 3/0482

FOREIGN PATENT DOCUMENTS

| CN | 105812469 A | 7/2016 |
| CN | 106302670 A | 1/2017 |
| CN | 106506502 A | 3/2017 |
| CN | 106557653 A | 4/2017 |
| CN | 106796593 A | 5/2017 |

* cited by examiner

METHOD AND SYSTEM FOR SYNCHRONOUSLY STORING MULTI-MODAL INFORMATION OF PORTABLE ENDOSCOPE

TECHNICAL FIELD

The present invention relates to the technical field of clinical diagnosis, and more specifically to a method and system for synchronously storing multi-modal information of a portable endoscope.

BACKGROUND

With the advent of information era, in order to enhance the informatization in various fields, past models in all walks of life have been changed, particularly in the hospital industry of global significance. Informatization improves the efficiency of medical information management for hospital administrators and doctors, and also helps patients to know their own conditions in real time. It is advantageous for the real-time communication of patients with doctors, and the difficulty of getting medical service is solved. The hospital information sharing and storage system has been applied in hospitals in China for more than a decade. The system has been developed rapidly from simple functions to complex functions and from stand-alone operation to networked operation. In terms of the range of application, the system is mainly used in paid applications. Such applications bring significant benefits to hospitals and also convenience to patients. Therefore, the system has been widely accepted by both hospitals and patients.

With the rapid development of communications, more application services become available in portable medical terminals. One of such services is a cloud backup storage service, by which a user can store contacts information, multimedia information, text information and the like in a terminal into a cloud server for backup. Accordingly, the loss of information stored in the terminal due to the loss or damage of the terminal can be prevented, and also it is convenient for transfer information to a new terminal. Therefore, various methods for storing a large amount of data into various storage environments such as a cloud and a server device and synchronizing the data with a personal terminal device have been widely applied. However, in the prior art, various synchronization methods work independently, rather than in a combined form.

Chinese Patent Application No. 201410853440.1 and Publication No. CN105530284A, entitled "FILE SYNCHRONIZATION METHOD", disclosed a file synchronization method for a terminal device, including the following steps of: judging whether there is a change in a file that is divided into a plurality of chunk files; if it is judged that there is a change in the file, calculating a hash value for each one of the divided chunk files; transmitting, to a server, a list of harsh values formed by the calculated harsh values; receiving a request to transmit chunk files corresponding to harsh values, which are not stored in the server, among the harsh values contained in the list of harsh values; and, in response to the transmission request, transmitting the chunk files to the server.

In the above synchronization solution, during the synchronization of media files acquired by a mobile medical device, for example, media files dominated during the synchronization of a portable endoscope, since no increment synchronization is involved, the complexity of synchronization will be increased if the files are processed indiscriminately by increment synchronization.

SUMMARY

In order to overcome or at least partially solve the above problems, the present invention provides a method and system for synchronously storing multi-modal information of a portable endoscope, which solve the problem of operation redundancy and increased synchronization complexity if the files are processed indiscriminately by increment synchronization when no increment synchronization is involved in the prior art.

According to one aspect of the present invention, a method for synchronously storing information is provided, including steps of:

S1: when a mobile terminal acquires data collected by a portable endoscope and updates local data with the acquired data, acquiring update record of the local data of the mobile terminal; and S2: when the mobile terminal is synchronized with a cloud, synchronizing data in the mobile terminal with data in the cloud by using the update record as information to be synchronized;

wherein, if the update record is not null, the data in the cloud is synchronized according to the information to be synchronized by using the local data in the mobile terminal as the latest data; or, if the update record is null, the local data in the mobile terminal is synchronized by using the data in the cloud as the latest data.

Preferably, in the step S1, the update record is recorded by a table to be synchronized, the information recorded in the table to be synchronized includes file information and file operation information during updating, and the operation information is recorded by an operation field.

Preferably, the step S1 of modifying a corresponding file according to an original operation field and recording file operation information in the table to be synchronized when the mobile terminal updates the local data specifically includes:

if the modified file does not exist in the table to be synchronized, inserting data of the modified file in the table to be synchronized, and changing the operation field of the modified file in the table to be synchronized to COPY; and if the modified file exists in the table to be synchronized, changing the operation field of the modified file in the table to be synchronized, wherein, if the original operation field of the modified file is DELETE, the operation field of the modified file in the table to be synchronized is changed to DELETE; and, if the original operation field of the modified file is MODIFY, the operation field of the modified file in the table to be synchronized is kept the same as the original operation field.

Preferably, the step S2 of synchronizing the data in the cloud according to the update record specifically includes:

finding a corresponding file according to the information recorded in the table to be synchronized, and performing a corresponding operation in the cloud according to the operation field of the file in the table to be synchronized.

Preferably, the step S2 of synchronizing the local data in the mobile terminal by using the data in the cloud as the latest data specifically includes:

comparing the data in the cloud with the local data in the mobile terminal, synchronizing data, which exists in the cloud but does not exist in the mobile terminal, to the mobile terminal; if data exists in both the cloud and the mobile terminal, comparing the synchronization time, and synchronizing the corresponding file in the cloud to the mobile terminal when the synchronization time is different.

Preferably, the step S2 further includes:

preferentially synchronizing a non-media file; and, if the file has been synchronized, deleting corresponding data from the table to be synchronized, and updating the synchronization time of the cloud; and after the synchronization has been completed, updating the synchronization time of the mobile terminal according to the synchronization time of the cloud.

A system for synchronously storing information is provided, including a mobile terminal configured to store local data and a cloud configured to store local data in the mobile terminal and perform information synchronization with the mobile terminal, and further including:

a table to be synchronized, configured to record information, including file information and file operation information during updating; and a synchronization module, configured to synchronize data in the mobile terminal with data in the cloud according to the information in the table to be synchronized; synchronize the data in the cloud according to the information to be synchronized by using the local data in the mobile terminal as the latest data if the table to be synchronized is not null; and, synchronize the local data in the mobile terminal by using the data in the cloud as the latest data if the table to be synchronized is null.

Preferably, the table to be synchronized records operation information of a file during the updating of local data:

if the modified file does not exist in the table to be synchronized, data of the modified file is inserted in the table to be synchronized, and the operation field of the modified file in the table to be synchronized is changed to COPY; or, if the modified file exists in the table to be synchronized, the operation field of the modified file in the table to be synchronized is changed, specifically: if the original operation field of the modified file is DELETE, the operation field of the modified file in the table to be synchronized is changed to DELETE; and, if the original operation field of the modified file is MODIFY, the operation field of the modified file in the table to be synchronized is kept the same as the original operation field.

Preferably, the mobile terminal further includes a first synchronization module, and the cloud includes a second synchronization module;

the first synchronization module is configured to record file information of the mobile terminal and perform synchronous modification according to the original operation field of the file in the mobile terminal; and the second synchronization module is configured to record file information of the cloud and perform synchronization according to the operation field of the corresponding file in the table to be synchronized during the synchronization with the mobile terminal.

Preferably, the synchronization module is configured to:

when the table to be synchronized is not null, synchronize the data in the cloud according to the operation field of the corresponding file in the table to be synchronized, and update the synchronization time of the mobile terminal according to the synchronization time after the data in the cloud has been synchronized; and when the table to be synchronized is null, compare the data in the cloud with the local data in the mobile terminal, synchronize data, which exists in the cloud but does not exist in the mobile terminal, to the mobile terminal, compare the synchronization time if data exists in both the cloud and the mobile terminal, and synchronize the corresponding file in the cloud to the mobile terminal when the synchronization time is different.

By the method and system for synchronously storing multi-modal information of a portable endoscope provided by the present invention, by creating a table to be synchronized to store change information and location information of files, selectively performing synchronization from the mobile terminal to a cloud or synchronization from the cloud to the mobile terminal according to whether or not the table to be synchronized is null during synchronization, and discriminately processing media files and non-media files during the synchronous storage process, the storage burden of the mobile terminal and the traffic for synchronization are both reduced.

DETAILED DESCRIPTION OF THE PRESENT INVENTION

The specific implementations of the present invention will be further described in detail by embodiments with reference to the accompanying drawings. The following embodiments are used for describing the present invention and not intended to limit the scope of the present invention.

Embodiment 1

Figure 1:
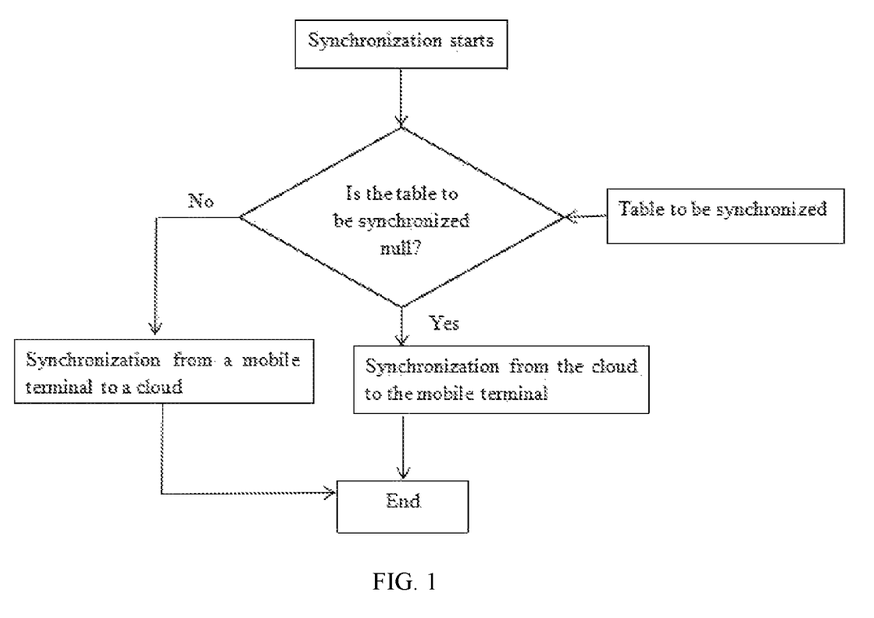
FIG. 1 is a specific flowchart of a method for synchronously storing information according to Embodiment 1 of the present invention.
Figure 2:
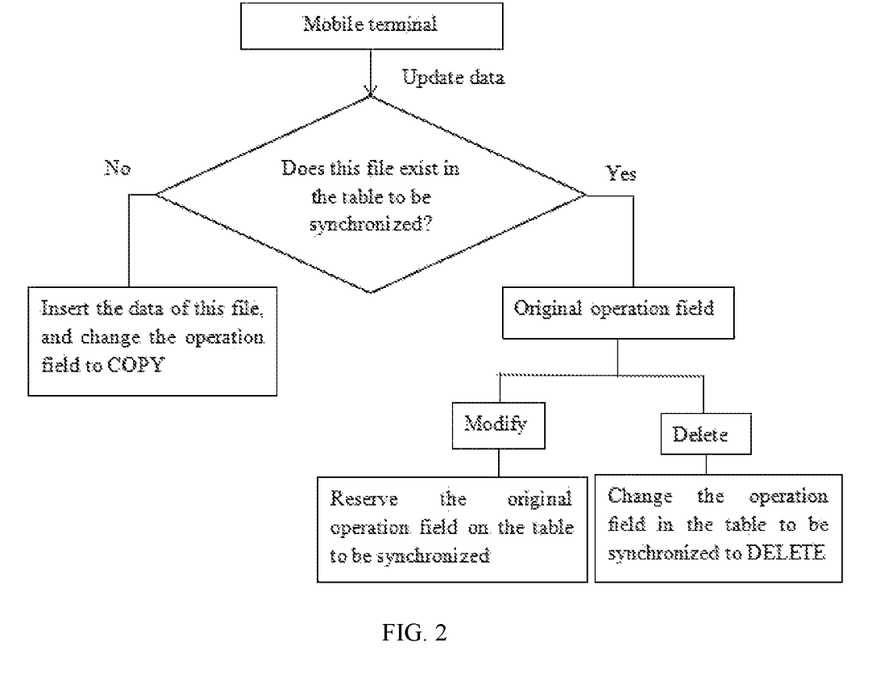
FIG. 2 is a flow block diagram of recording operation information of a file in a table to be synchronized according to Embodiment 1 of the present invention.
Figure 3:
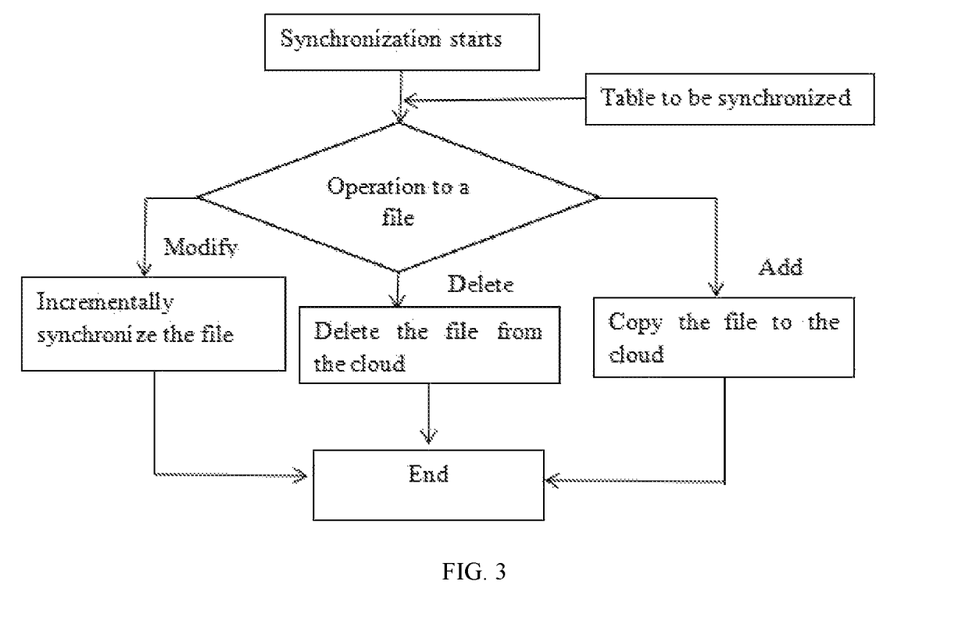
FIG. 3 is a schematic flowchart of synchronization from a mobile terminal to a cloud according to Embodiment 1 of the present invention.
Figure 4:
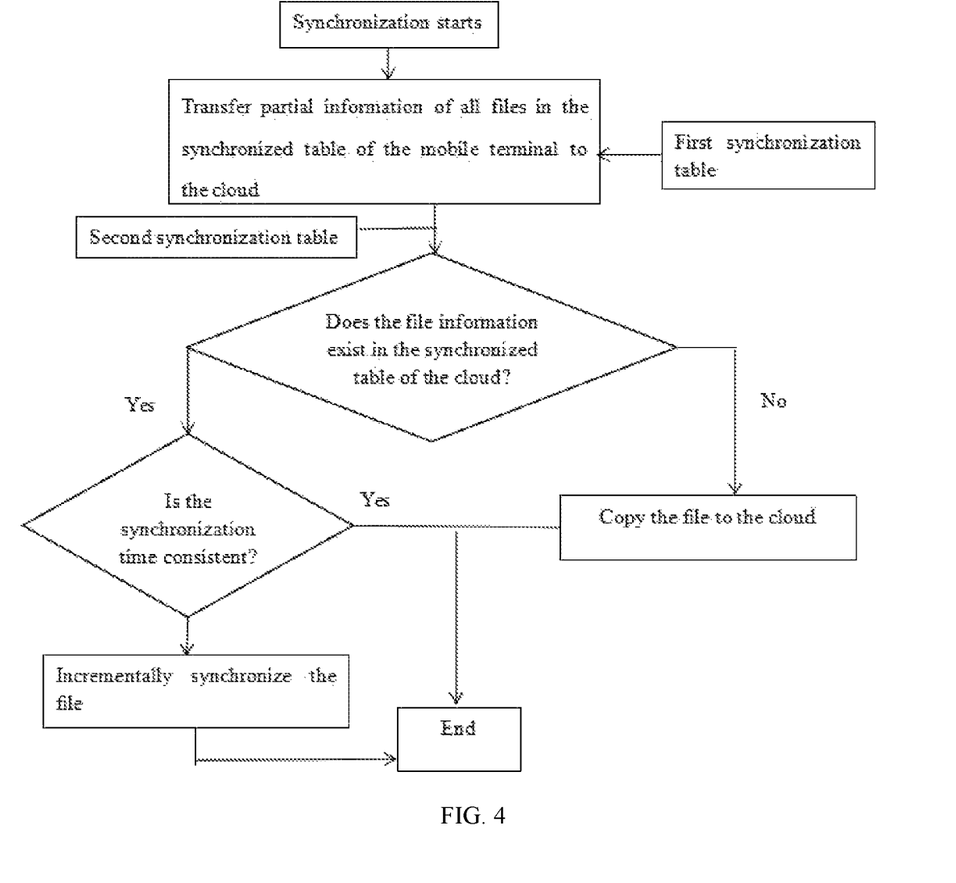
FIG. 4 is a schematic flowchart of synchronization from a cloud to a mobile terminal according to Embodiment 1 of the present invention.

As shown in FIGS. 1-3, a method for synchronously storing information is provided, including steps of:

S1: when a mobile terminal acquires data collected by a portable endoscope and updates local data with the acquired data, acquiring update record of the local data of the mobile terminal; and S2: when the mobile terminal is synchronized with a cloud, synchronizing data in the mobile terminal with data in the cloud by using the update record as information to be synchronized;

wherein, if the update record is not null, the data in the cloud is synchronized according to the information to be synchronized by using the local data in the mobile terminal as the latest data; or, if the update record is null, the local data in the mobile terminal is synchronized by using the data in the cloud as the latest data.

As shown in FIG. 1, the update record of the local data in the mobile terminal is recorded by a table to be synchronized, and the operation information of the local data is recorded by an operation field, specifically including DELETE, MODIFY and ADD. During the specific process, if this data exists in the mobile terminal, an operation field in the table to be synchronized needs to be adjusted according to the operation field of the local data in the mobile terminal. If the operation to this file is a delete operation at this time, the value of the original operation field is changed to DELETE and then reserved in the table to be synchronized. If the operation to this file is a modify operation at this time, the value of the original operation field is unchanged and reserved in the table to be synchronized. If this data does not exist in the terminal, this data will be directly added in the table to be synchronized and the operation field of this data in the table to be synchronized is changed to COPY. In this way, during the synchronization with the cloud, the corresponding data is directly copied to the cloud. During the synchronization of the mobile terminal and the cloud, it is only required to check whether the table to be synchronized is null, and the synchronization can be realized according to the operation field of the corresponding file in the table to be synchronized. As shown in FIG. 1, if the information to be synchronized is not null, the data in the cloud is synchronized according to the information to be synchronized by using the local data in the mobile terminal as the latest data.

If the information to be synchronized is null, the local data in the mobile terminal is synchronized by using the data in the cloud as the latest data.

In this embodiment, during the modification of a local file in the mobile terminal, a table is created to record modification information as the information to be synchronized.

Preferably, in the step S1, the information to be synchronized is recorded by the table to be synchronized, and the field in the table to be synchronized includes a user's file ID, patient's folder name, file name, file type (media file (0) and non-media file (1)), and operation (ADD (0), MODIFY (1) and DELETE (2)).

In this embodiment, the local data in the mobile terminal and the data in the cloud are stored in files. When the local data in the mobile terminal is modified and if the modified file does not exist in the table to be synchronized, the data of this file is inserted in the table to be synchronized. If the modified file exists in the table to be synchronized, the value of the operation field of this file in the table to be synchronized is changed according to the actual situation. If the operation to the file is a delete operation at this time, the value of the original operation field is changed to DELETE; and, if the operation to the file is a modify operation at this time, the value of the original operation field remains unchanged.

In this embodiment, the synchronization of the mobile terminal and the cloud can be realized by cooperating a first synchronized table in the mobile terminal and a second synchronized table in the cloud with the table to be synchronized. All the first synchronized table, the second synchronized table and the table to be synchronized are in a same account.

The field in the first synchronized table includes file ID, and patient's folder name, file name, file type (media file (0) and non-media file (1)), and synchronization time (1990-01-01 00:00:00 by default). Every time a new file is added, corresponding data is added in this table; and if a file is deleted, corresponding data is deleted from this table. This is applicable to the modify operation.

The field in the second synchronized table includes: file ID, file name, file type (media file (0) and non-media file (1)), and synchronization time.

Preferably, as shown in FIG. 2, the step S2 of synchronizing the data in the cloud according to the information to be synchronized specifically includes:

finding a corresponding file according to the information in the table to be synchronized, and synchronizing the data in the cloud according to the value of the operation field; if the original operation field modified for the first synchronized table is "ADD", copying the added file to the second synchronized table according to the operation field "COPY" in the table to be synchronized; and, if the original operation field modified for the first synchronized table is "DELETE", deleting the data of the corresponding file from the synchronized table in the cloud.

In this embodiment, the non-media file is synchronized preferentially, followed by the media file. If the file has been synchronized, the corresponding data is deleted from the table to be synchronized, and the synchronization time of the cloud is updated; and, if the synchronization is related to a delete operation, the data of the corresponding file is deleted from the synchronized table of the cloud.

After the data synchronization of the cloud has been completed, the synchronization time of the mobile terminal is updated according to the synchronization time of the cloud.

Preferably, as shown in FIG. 3, the step S2 of synchronizing the local data in the mobile terminal by using the data in the cloud as the latest data specifically includes:

comparing the data in the cloud with the local data in the mobile terminal; synchronizing data, which does not exist in the mobile terminal, to the mobile terminal, comparing the synchronization time if this data exists in both the cloud and the mobile terminal, and synchronizing the corresponding file in the mobile terminal if the synchronization time is different.

The non-media file is synchronized preferentially, followed by the media file.

The synchronization time of the corresponding files in the mobile terminal and the cloud is updated.

The method in this embodiment is applicable to the management of patients' cases. By the method for synchronously storing information in this embodiment, by acquiring patients' case information and storing the patients' case information to the cloud, the patients' case information can be effectively stored, and the historical patients' case information stored in the cloud, which has been recently updated, can also be acquired during usage.

Embodiment 2

This embodiment describes a system for synchronously storing information, which is used for storing multi-modal information of a portable endoscope system by the method described in Embodiment 1. In the system in this embodiment, patients' symptom information (in media files and non-media files) is acquired by a portable endoscope in combination with an intelligent mobile terminal. By recording the operation to a file and the file type, the patients' symptom information is discriminately processed during the storage and synchronization, so that the storage burden of the intelligent mobile terminal and the traffic for synchronization are reduced, and the storage of endoscopic diagnosis information and the synchronization of endoscopic diagnosis information with the cloud are realized. During the synchronization, three tables under an account are mainly used, i.e., a synchronized table and a table to be synchronized in the mobile terminal and a synchronized table in the cloud. The table to be synchronized is mainly used during the synchronization of files in the mobile terminals to the cloud, and the files recorded in the table to be synchronized are synchronized to the cloud according to the actual situation. The synchronized table in the mobile terminal and the synchronized table in the cloud are mainly used during the synchronization of files in the cloud to the mobile terminal. By comparing the two synchronized tables, a file that does not exist in the mobile terminal or is to be incrementally synchronized is found.

Specifically including:

Storage

In the mobile terminal, a folder, named by abbreviation of a patient's name+the timestamp when the folder is created, is created for the patient, including a folder containing media files and a folder containing non-media files. The folders contain corresponding files, respectively.

Synchronization

There are two tables (i.e., a synchronized table and a table to be synchronized) for each account in the mobile terminal.

The field in the synchronized table includes file ID, patient's folder name, file name, file type (media file (0) and non-media file (1)), and synchronization time (1990-01-01 00:00:00 by default in this embodiment). Every time a new file is added, corresponding data is added in this table; and if a file is deleted, corresponding data is deleted from this table. This is applicable to the modify operation.

The field in the table to be synchronized includes: file ID, patient's folder name, file name, file type (media file (0) and non-media file (1)), and operation (ADD (0), MODIFY (1) and DELETE (2)).

During the modification of the information about a patient in this mobile terminal, if the modified file does not exist in the table to be synchronized, the data of this file is inserted in the table to be synchronized; if the modified file exists in the table to be synchronized, the value of the operation field of this file in the table to be synchronized is changed according to the actual situation; if the operation to the file is a delete operation at this time, the value of the original operation field is changed to DELETE; and, if the operation to the file is a modify operation at this time, the value of the original operation field remains unchanged.

There is a table (i.e., a synchronized table) for each account in the cloud. The field in the synchronized table includes file ID, folder name, file type (media file (0) and non-media file (1)), and synchronization time.

During the synchronization:

If the table to be synchronized is not null (from the mobile terminal to the cloud), a corresponding file is quickly found according to the information in the table to be synchronized, and a corresponding synchronization method is used according to the value of the operation field (if the operation is an add operation, copying is performed; if the operation is a modify operation, increment synchronization is performed; and, if the operation is a delete operation, the corresponding file is deleted). The non-media file is synchronized preferentially. When a certain file has been uploaded and synchronized, the corresponding data is deleted from the table to be synchronized, and the synchronization time of the corresponding file in the synchronized table of the cloud is updated. If the synchronization is related to a delete operation, the data of the corresponding file in the synchronized table in the cloud is deleted. The synchronization time in the synchronized table in the mobile terminal is updated (by using the value of the synchronization time of the synchronized table in the cloud).

If the table to be synchronized is null, the data in the cloud now is the latest data (from the cloud to the mobile terminal). The field information in the synchronized table of the mobile terminal, which is the same as that in the synchronized table of the cloud, is extracted and then transferred to the cloud to compare the synchronized table of the mobile terminal with the synchronized table of the cloud. If there is data that exists in the synchronized table of the cloud but does not exist in the synchronized table of the mobile terminal, the corresponding file in the cloud is synchronized to the mobile terminal. If the data exit in both the synchronized table of the cloud and the synchronized table of the mobile terminal, the synchronization time is compared. If the synchronization time is different, the corresponding file in the mobile terminal is synchronized; and, if the synchronization time is the same, no operation is performed. If the file is a media file, synchronous replication is performed; and, if the file is a non-media file, increment synchronization or synchronous replication is performed according to the actual situation. Since the media file is too large in size, the non-media file is preferentially synchronized, followed by the metadata and thumbnails of the media file. In order to reduce the storage burden of the mobile terminal and the traffic and time for synchronization, the synchronization of the media file can be selectively performed according to the patient. Finally, the synchronization time of the corresponding files in the synchronized table of the mobile terminal and the synchronized table of the cloud are updated (if the synchronization is related to a delete operation, the data of the corresponding file in the synchronized table of the cloud is deleted).

In order to ease the burden due to a too large amount of data during the synchronization, in this embodiment, the synchronization is automatically performed when it is detected that the mobile terminal is connected to wiff.

In conclusion, the method of the present application is merely a preferred implementation and not intended to limit the protection scope of the present invention. Any modifications, equivalent replacements and improvements made within the spirit and principle of the present invention shall fall into the protection scope of the present invention.

What is claimed is:

1. A method of synchronously storing information, comprising steps of:

S1: acquiring an update record of local data of a mobile terminal when the mobile terminal acquires data collected by a portable endoscope and updates the acquired data to the local data wherein the mobile terminal stores a first synchronized table recording synchronization done in the mobile terminal and a table to be synchronized, and the update record is recorded in the table to be synchronized; and S2: synchronizing data in the mobile terminal with data in a cloud-based server using the update record, wherein the cloud-based server stores a second synchronized table recording synchronization done in the cloud-based server, and wherein synchronizing data in the mobile terminal with data in the cloud-based server comprises:

determining that the table to be synchronized is not null, and synchronizing the data in the cloud-based server with the local data in the mobile terminal according to the table to be synchronized stored in the mobile terminal; and determining that the table to be synchronized is null, and synchronizing the local data in the mobile terminal with the data in the cloud-based server, comprising extracting fields in the first synchronized table of the mobile terminal, which are also present in the second synchronized table of the cloud-based server, transferring the extracted fields to the cloud-based server, comparing the transferred fields with those in the second synchronized table to obtain a difference between the first synchronized table of the mobile terminal and the second synchronized table of the cloud-based server, and synchronizing the local data in the mobile terminal according to the difference;

wherein:

the information recorded in the table to be synchronized comprises file information and file operation information during updating; wherein operation information is recorded by an operation field;

if the file is a media file, synchronous replication is performed; if the file is a non-media file, increment synchronization or synchronous replication is performed according to an actual situation, and the non-media file is preferentially synchronized followed by the media file;

if the file has been synchronized, corresponding data is deleted from the table to be synchronized, and a synchronization time of the cloud-based server is updated; and after synchronization has been completed, a synchronization time of the mobile terminal is updated according to the synchronization time of the cloud-based server.

2. The method for synchronously storing information according to claim 1, wherein the step S1 further comprises:

modifying a file according to an original operation field and recording file operation information in the table to be synchronized when the mobile terminal updates the local data; if the modified file does not exist in the table to be synchronized, inserting data of the modified file in the table to be synchronized, and changing an operation field of the modified file in the table to be synchronized to COPY; and if the modified file exists in the table to be synchronized, changing the operation field of the modified file in the table to be synchronized, wherein if the original operation field of the modified file is DELETE, the operation field of the modified file in the table to be synchronized is changed to DELETE; and if the original operation field of the modified file is MODIFY, the operation field of the modified file in the table to be synchronized is kept same as the original operation field.

3. The method for synchronously storing information according to claim 2, wherein the step S2 of synchronizing the data in the cloud-based server according to the update record further comprises:

finding a corresponding file according to the information recorded in the table to be synchronized, and performing a corresponding operation in the cloud-based server according to the operation field of the file in the table to be synchronized.

4. The method for synchronously storing information according to claim 3, wherein the step S2 of synchronizing the local data in the mobile terminal by using the data in the cloud as the latest data further comprises:

comparing the data in the cloud-based server with the local data in the mobile terminal;

synchronizing data existed in the cloud-based server and not in the mobile terminal, to the mobile terminal;

comparing a synchronization time if data exists in both the cloud-based server and the mobile terminal, and synchronizing the corresponding file in the cloud-based server to the mobile terminal, if the synchronization time of the cloud-based server and of the mobile terminal is different.

5. A system for synchronously storing information, comprising a mobile terminal configured to store local data and acquire an update record of local data upon receipt of data collected from a portable endoscope, and a cloud-based server configured to perform information synchronization with the mobile terminal when connected to the mobile terminal, the system comprising:

a table to be synchronized, configured to record information comprising file information and file operation information during updating; and a synchronization module configured to synchronize data in the mobile terminal with data in the cloud-based server according to the table to be synchronized, to synchronize the data in the cloud-based server with the local data in the mobile terminal according to the table to be synchronized in case of determining that the table to be synchronized is not null, and to synchronize the local data in the mobile terminal with the data in the cloud-based server in case of determining that the table to be synchronized is null by: extracting fields in the first synchronized table of the mobile terminal, which are also present in the second synchronized table of the cloud-based server, transferring the extracted fields to the cloud-based server, comparing the transferred fields with those in the second synchronized table to obtain a difference between the first synchronized table of the mobile terminal and the second synchronized table of the cloud-based server, and synchronizing the local data in the mobile terminal according to the difference, wherein the first synchronized table records synchronization done in the mobile terminal, and the second synchronized table records synchronization done in the cloud-based server;

wherein the update record of the local data in the mobile terminal is recorded by the table to be synchronized, the information recorded in the table to be synchronized comprises file information and file operation information during updating, and the file operation information is recorded by an operation field; if the file is a media file, synchronous replication is performed; if the file is a non-media file, increment synchronization or synchronous replication is performed according to the actual situation, and the non-media file is preferentially synchronized followed by the media file; if the file has been synchronized, a corresponding data is deleted from the table to be synchronized, and a synchronization time of the cloud-based server is updated; and, after the synchronization has been completed, a synchronization time of the mobile terminal is updated according to the synchronization time of the cloud-based server.

6. The system for synchronously storing information according to claim 5, wherein, when the table to be synchronized records the file operation information during the updating of the local data in the mobile terminal:

if the modified file does not exist in the table to be synchronized, data of the modified file is inserted in the table to be synchronized, and the operation field of the modified file in the table to be synchronized is changed to COPY; or if the modified file exists in the table to be synchronized, the operation field of the modified file in the table to be synchronized is changed; wherein if the original operation field of the modified file is DELETE, the operation field of the modified file in the table to be synchronized is changed to DELETE; and, if the original operation field of the modified file is MODIFY, the operation field of the modified file in the table to be synchronized is kept same as the original operation field.

7. The system for synchronously storing information according to claim 6, wherein the mobile terminal comprises a first synchronization module, and the cloud-based server comprises a second synchronization module; and wherein:

the first synchronization module is configured to record file information of the mobile terminal and perform synchronous modification according to the original operation field of the file in the mobile terminal; and the second synchronization module is configured to record file information of the cloud-based server and perform synchronization according to the operation field of the corresponding file in the table to be synchronized during the synchronization with the mobile terminal.

8. The system for synchronously storing information according to claim 6, wherein the synchronization module is configured to:

synchronize the data in the cloud-based server according to the operation field of the corresponding file in the table to be synchronized when the table to be synchronized is not null, and update the synchronization time of the mobile terminal according to the synchronization time after the data in the cloud-based server has been synchronized; and compare the data in the cloud-based server with the local data in the mobile terminal when the table to be synchronized is null, synchronize data existed in the cloud-based server and not in the mobile terminal with the local data in the mobile terminal, compare the synchronization time if data exists in both the cloud and the mobile terminal, and synchronize the corresponding file in the cloud-based server to the mobile terminal when a synchronization time of the cloud-based server and of the mobile terminal is different.

* * * * *

UNITED STATES PATENT AND TRADEMARK OFFICE
CERTIFICATE OF CORRECTION

PATENT NO. : 10,664,494 B2
APPLICATION NO. : 16/049709
DATED : May 26, 2020
INVENTOR(S) : Shuai Ding et al.

It is certified that error appears in the above-identified patent and that said Letters Patent is hereby corrected as shown below:

On the Title Page

Item (73) Assignee: should read:
--(73) Assignees: Hefei University of Technology     Hefei, China;
              Hefei DVL Electron Co., Ltd.     Hefei, China--

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*